(12) United States Patent
Sorrentino et al.

(10) Patent No.: US 7,094,981 B2
(45) Date of Patent: Aug. 22, 2006

(54) POWERED TOOTHBRUSH WITH TEST BUTTON

(75) Inventors: Alan V. Sorrentino, Cranbury, NJ (US); Robert Moskovich, East Brunswick, NJ (US)

(73) Assignee: Colgate-Palmolive Company, New York, NY (US)

( * ) Notice: Subject to any disclaimer, the term of this patent is extended or adjusted under 35 U.S.C. 154(b) by 65 days.

(21) Appl. No.: 10/763,621

(22) Filed: Jan. 23, 2004

(65) Prior Publication Data

US 2005/0161313 A1 Jul. 28, 2005

(51) Int. Cl.
*H01H 9/00* (2006.01)
*H01H 35/00* (2006.01)
*A61C 17/16* (2006.01)
*B65D 83/00* (2006.01)

(52) U.S. Cl. .................. 200/332.2; 15/22.1; 200/52 R; 200/61.58 R; 206/362.2

(58) Field of Classification Search .................. 15/22.1, 15/28; 200/16 R, 16 A, 16 D, 42.01, 52 R, 200/60, 61.58 R, 61.42, 293.1, 329–332.2, 200/302.2, 538; 206/362.2

See application file for complete search history.

(56) References Cited

U.S. PATENT DOCUMENTS

| | | | |
|---|---|---|---|
| 2,477,274 A | 7/1949 | Trecek | |
| 3,167,624 A | 1/1965 | Jones, Jr. | |
| 3,489,936 A * | 1/1970 | Boyles | 200/332.2 X |
| 4,225,994 A * | 10/1980 | Stoltz | 200/330 X |
| 4,804,984 A | 2/1989 | Heuer et al. | |
| 4,925,025 A | 5/1990 | Anten et al. | |
| 5,188,222 A | 2/1993 | Pierce | |
| 5,494,252 A | 2/1996 | Amit et al. | |
| 5,625,916 A | 5/1997 | McDougall | |
| 5,772,031 A | 6/1998 | Landis | |
| 6,000,083 A | 12/1999 | Blaustein et al. | |
| D425,414 S | 5/2000 | Baker et al. | |
| 6,189,693 B1 | 2/2001 | Blaustein et al. | |
| 6,311,837 B1 | 11/2001 | Blaustein et al. | |
| D455,071 S | 4/2002 | Ruben | |
| 6,371,294 B1 | 4/2002 | Blaustein et al. | |
| 6,564,940 B1 | 5/2003 | Blaustein et al. | |
| 2001/0004781 A1 | 6/2001 | Blaustein et al. | |
| 2001/0022277 A1 | 9/2001 | Blaustein et al. | |
| 2002/0017474 A1 | 2/2002 | Blaustein et al. | |
| 2002/0020645 A1 | 2/2002 | Blaustein et al. | |
| 2002/0029988 A1 | 3/2002 | Blaustein et al. | |
| 2002/0032941 A1 | 3/2002 | Blaustein et al. | |
| 2002/0038772 A1 | 4/2002 | Blaustein et al. | |
| 2002/0078514 A1 | 6/2002 | Blaustein et al. | |
| 2002/0124333 A1 | 9/2002 | Hafliger et al. | |
| 2003/0000031 A1 | 1/2003 | Zhuan | |
| 2003/0066145 A1 | 4/2003 | Prineppi | |
| 2003/0135940 A1 | 7/2003 | Lev et al. | |
| 2003/0205492 A1 | 11/2003 | Ferber et al. | |
| 2003/0221267 A1 | 12/2003 | Chan | |

FOREIGN PATENT DOCUMENTS

| | | |
|---|---|---|
| EP | 0 587 406 A2 | 3/1994 |
| JP | 402109226 A | 4/1990 |

\* cited by examiner

*Primary Examiner*—Richard K Lee
(74) *Attorney, Agent, or Firm*—Harris A. Wolin

(57) ABSTRACT

A powered operating device such as a powered toothbrush includes a test button for momentarily testing the operability of the device. The test button simultaneously presses against both the on portion and the off portion of the switch which controls the operation of the device. While pressure is applied to the test button, the device is placed in its operative condition and when the pressure is released, the geometric structure of the test button held by the package releases the on portion of the switch at the same time or just before the off portion. Thus, assuring that the switch turns off.

20 Claims, 2 Drawing Sheets

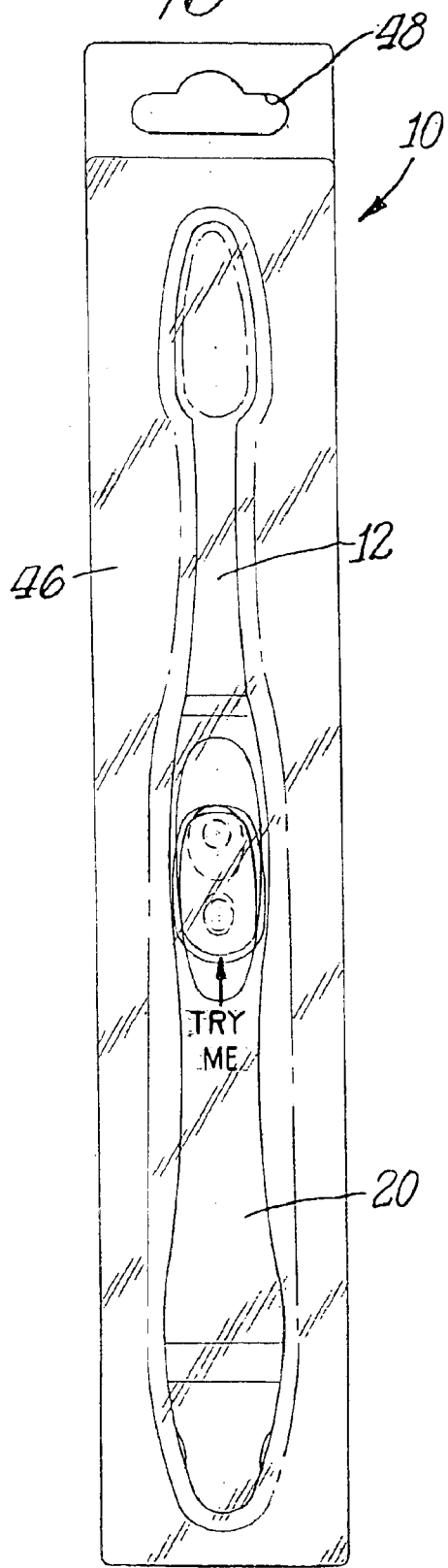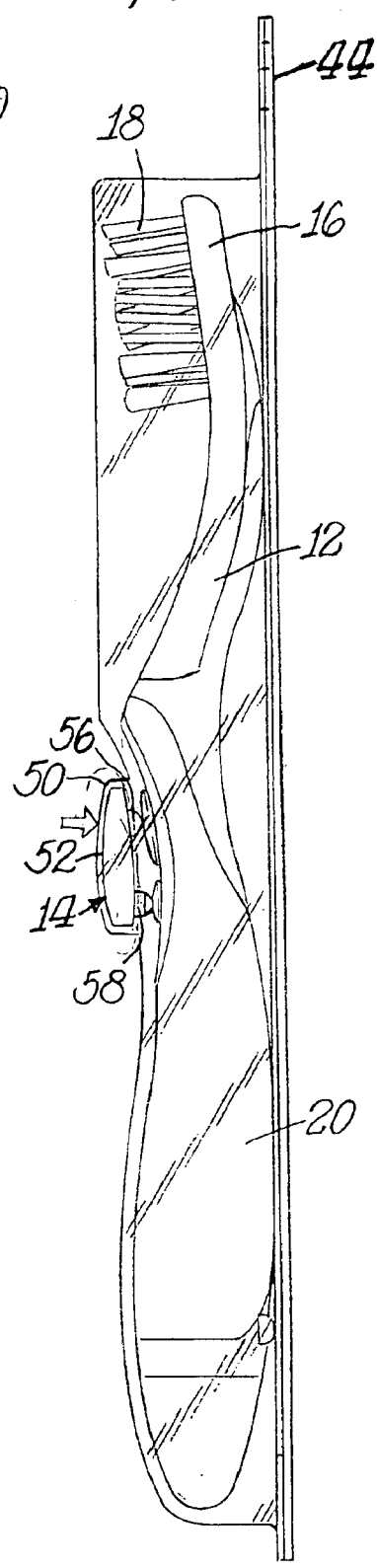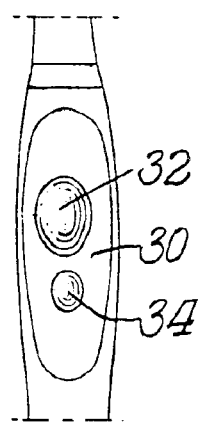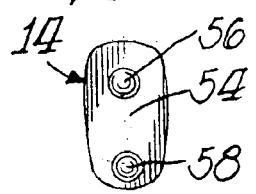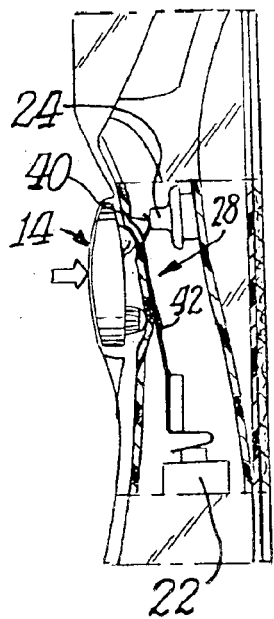

POWERED TOOTHBRUSH WITH TEST BUTTON

BACKGROUND OF THE INVENTION

For some powered items, such as a powered toothbrush, it is preferable for the consumer to be able to try to experience the function of the item before a purchase is made. Many powered items use a spring switch to provide the item with the ability to be turned on and off. In normal use of such items the user will press the "on" portion of the switch to activate and set the switch in the on position. Once in the on position the switch remains in this position until the "off" position is depressed to set the spring switch in the off position. Various attempts have been made to provide test structure, frequently referred to as "try me", in order to permit the user to test the operation of the item.

Some attempts have been made in the field of power toothbrushes to permit a prospective purchaser of a powered toothbrush to test the operability of the toothbrush. One of the concerns is that the testing should be of a momentary nature so that a tested toothbrush will not remain in its on or operating condition after the test. One approach that has been taken is to use a pressing movement of the switch for the momentary actuation and a sliding movement for the continuous operation. Examples of this approach are found in U.S. Pat. Nos. 6,000,083, 6,189,693, 6,311,837, 6,371,294 and 6,564,940 and U.S. Published Patent Application Nos. 2001/0004781, 2001/0022277, 2002/0020645, 2002/0032941, 2002/0038772 and 2002/0078514. A disadvantage with this type of approach is that the user is required to use different motions for either testing or continuously operating the toothbrush.

A further approach at providing only momentary actuation for test purposes of a power toothbrush is to provide separate switches, one switch being for the test purposes giving momentary actuation and the other switch being for continuous operation. Examples of this approach are found in U.S. Published Application Nos. 2002/0017474 and 2002/0029988. A disadvantage with this approach is that the user must be careful as to which switch is being actuated. Other examples of providing power testing of toothbrushes and the like are found in U.S. Pat. Nos. 4,925,025, 5,118,222 and 5,494,252 and in U.S. Published Application Nos. 2003/0000031, 2003/0066145, 2003/0135940 and 2003/0205492. Other examples include European Patent Application EP 0 587 406 and Japanese Application JP 402109226.

SUMMARY OF THE INVENTION

An object of this invention is to provide a toothbrush which includes a test button for permitting a user to confirm the operability of the device.

A further object of this invention is to provide such a device having switch structure which includes an on position for continuously operating the device and an off position for inactivating the device.

A further object of this invention is to apply such techniques for the testing of the operation of a powered toothbrush.

In accordance with this invention a powered operating device has a movable section which is moved in response to power transmitting structure from a power source. The device includes a switch structure having an on position for activating the power transmitting structure so that the movable section is in continuous operation until inactivated by actuation of the switch structure at an off position. A test button is provided for simultaneously contacting both the on position and the off position of the switch structure when pressure is applied to the test button. This is accomplished in such a manner that while such pressure is being applied, the switch structure on position is activated to permit operation of the powered operating device. However, upon the release of pressure because the test button had also been in contact with the switch structure at the off position the device is immediately inactivated.

In a preferred practice of this invention the switch structure is a spring of a rocker type nature wherein one portion of the spring would be pushed into contact with an electrical contact pin when in the on position and would remain in that position until another portion of the spring is depressed at the off position to move the on position portion of the spring away from the contact pin. The test button functions in such a manner than when it is pressed against the spring the spring tends to flatten while the pressure is being applied which causes contact between the on position portion of the spring and the contact pin while still applying pressure at the off position. Upon release of the test button the spring resumes only its off position condition wherein the on position portion no longer contacts the contact pin.

In a preferred practice of the invention the powered operating device is a powered toothbrush having cleaning elements such as bristles on a movable section of the cleaning head. The toothbrush could be packaged in a bubble container which is flexible in at least the portion of the bubble having the test button so that the test button could be pressed and moved into contact with the switch structure by the application of pressure from the outside of the package.

THE DRAWINGS

FIG. 1 is a front elevational view of a powered operating device in the form of a toothbrush housed in a package in accordance with this invention;

FIG. 2 is a side elevational view of the device shown in FIG. 1;

FIG. 3 is a fragmental front elevational view of the toothbrush shown in FIGS. 1–2 illustrating the external portion of the switch structure;

FIG. 4 is a rear elevational view of the test button shown in FIGS. 1–2;

FIGS. 5 and 6 are fragmental partial cross-sections showing the toothbrush of FIGS. 1–2 in different modes of test operation;

DETAILED DESCRIPTION

Figure 8:
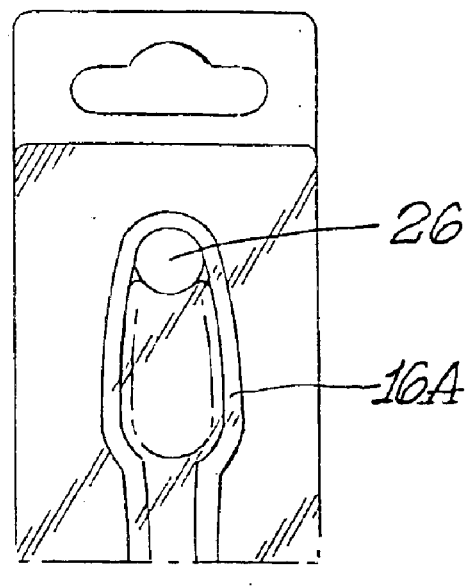
FIG. 8 is a front elevational view showing a modified form of cleaning head for a toothbrush in accordance with this invention.

FIGS. 1–2 illustrate an assembly 10 in accordance with this invention wherein a powered operating device 12 is provided with a test button 14 so that a potential purchaser of the device or other user may confirm the operability of the device 12. In the illustrated form the device 12 is a toothbrush. It is to be understood, however, that the invention may be practiced with other types of powered operating devices. In general, such powered operating devices would include a movable section which for the toothbrush 12 is located in the cleaning head 16 having outwardly extending cleaning elements such as bristles 18. The toothbrush 12 also includes a hollow handle 20. Mounted within the handle 20 is a suitable power source such as a battery 22 as shown in FIG. 5. The battery operates the movable section of the cleaning head 16 through any suitable power transmitting structure which includes electrical contact pin 24. In the illustrated version of the toothbrush 12 shown in FIGS. 1–2 the movable section is a vibratory type of movement of the bristles. An example of such type of motion is described in U.S. Published Application 2002/0124333 all of the details of which are incorporated herein by reference thereto. Any other type of movement, however, may be used in accordance with this invention. Thus, FIG. 8 illustrates a cleaning head 16A which includes a disk-like movable section 26 which could, for example, be oscillated back and forth in a rotational manner by a drive mechanism, such as shown in U.S. Pat. No. 5,625,916, all of the details of which are incorporated herein by reference thereto.

Figure 6:
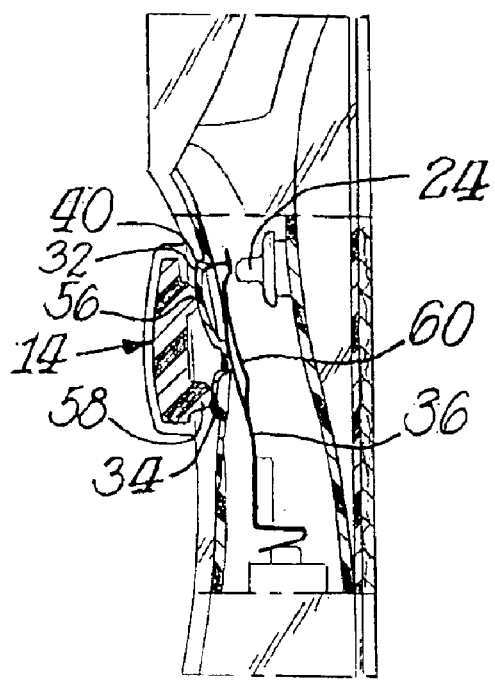
Figure 7:
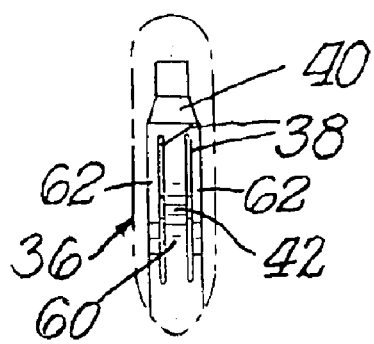
FIG. 7 is a front elevational view showing the internal switch structure used in the toothbrush of FIGS. 1–2.

The power transmitting structure for operating the movable section is controlled by a switch structure 28. FIG. 3 illustrates the outer portion of the hollow handle 20 to have a flexible wall 30. One location of the wall 30 has an outward protrusion 32 which is at the on position of the switch structure. Another smaller outward protrusion 34 is at the off position of the switch structure. FIGS. 5–7 illustrate the details of the main portion of the switch structure which is a spring switch 36 of a rocker type construction. As shown in FIG. 7 the spring switch 36 has a pair of slits 38,38 creating a movable central portion 60 and a pair of side portions 62,62. Spring 36 also includes an outer movable free end 40. When the outer end 40 of spring 36 is pressed, the outer end 40 contacts electrical contact pin 24 to activate the power transmitting structure for moving the movable section of the powered operated device such as the movable section of the cleaning head 16. In this condition central portion 60 is rocked outwardly of side portions 62. When the off location portion 40 of spring 36 is activated, the on portion 40 is moved away from and out of contact with electrical contact pin 24 thereby inactivating the power transmitting structure. Central portion 60 is rocked inwardly of side portions 62. This position is shown in FIG. 6. Ordinarily, in the normal operation of toothbrush 12 the on button 32 would be pressed to push spring portion 40 to bend the spring 36 so that its on location portion 40 makes electrical contact with contact pin 24 and remains in contact with contact pin 24 thereby resulting in continuous operation of the movable section of toothbrush 12. The continuous operation is halted when the off button portion 34 is pressed to push portion 42 of central portion 60 back to the position shown in FIG. 6. The end 40 of spring 36 flexes away from and out of contact with contact pin 24 to inactivate the power transmitting structure so that the movable section no longer moves.

Advantageously the test procedure will work regardless of what portion of test button 14 is pressed. As long as pressure is applied to any location of the outer surface 52 of test button 14, the entire rigid test button 14 will move inwardly pressing against both on and off buttons 32,34. Spring 36 is flattened to result in on portion 40 contacting pin 24. In this flattened condition of spring 36, the tendency for spring 36 to return to its off position is overcome by the inward pressing of test button 14. Spring 36, then returns to its off position shown in FIG. 6 upon the removal of the pressure.

The toothbrush 12 may be packaged in any suitable manner. In the embodiment illustrated herein the package includes a generally stiff backing member 44 which could be made of cardboard, stiff plastic or any other suitable material. A transparent plastic blister 46 is mounted to backing 44 to completely enclose the toothbrush 12 yet permit the toothbrush to be visible. The backing and bubble laminate at the upper end of the package may include a cut-out 48 so that the package could be hung for display purposes. One portion of the bubble 46 has an outward offset 50 as shown in FIG. 2. The outward offset 50 is located at the switch structure. Also located in this offset portion is the test button 14. Test button 14 may be made of any suitable material and may be of any suitable shape. In the illustrated embodiment test button 14 is a stiff plate or block having a generally convex outer surface 52 and a generally concave inner surface 54. A pair of activating posts 56,58 extend outwardly from inner surface 54. Activating pin 58 is longer than activating pin 56. As a result, when in the normal packaged condition activating pin 56 makes slight non-pressure contact with the on location button 32 while activating pin or post 58 makes slight non-pressure contact with the off location button 34. This condition is also illustrated in FIG. 6.

When it is desired to test the operability of the toothbrush 12, pressure is applied against test or activation button 14 as shown in FIG. 5. This results in the pressure being applied simultaneously to both the on and off buttons 32,34 and to the on and off position 40,42 of the switch structure which flattens the spring 36 so that contact is made between the on position 40 and electrical contact pin 24 to activate the power transmitting structure thus causing operation of the movable section. When the pressure is released, because central portion 60 at its off location 42 had also been under pressure, the spring 36 snaps back to the position shown in FIG. 6 with the on position 40 out of contact with electrical contact pin 24. As a result, the device or toothbrush 12 can be momentarily operated, when in the condition of FIG. 5, assuring that the device is restored to the "off" position by the consumer simply letting go of the package. Battery life will thereby be preserved without the consumer consciously having to turn the device off.

Once the device is purchased the device is removed from the package and the test button 14 can be discarded. Thereafter the switch structure would be activated, as previously discussed, by either selectively pressing the on button 32 or the off button 34. When the on button 32 is pressed the outer portion 40 of spring 36 is moved into contact with the electrical contact pin 24 and the operation of the movable section is initiated and remains continuously on. When it is desired to inactivate the operation the off button 34 is pressed. This causes the central portion 60 of the spring to flex so that the on location portion 40 is moved out of contact with the electrical contact pin 24. The spring 36 remains in this off condition until the on button 32 is again pressed.

Because the on activating button 32 and the off activating button 34 are integral parts of the resilient wall 30; the buttons may be depressed inwardly from their normal position shown in FIG. 2 a sufficient distance to contact the spring 36. Upon release the buttons 32,34 then return to their normal position. In the meantime, however, by pressing either button 32 or 34 the contact made with the spring 36 cause the spring to rock to its appropriate on or off position.

The present invention has distinct advantages over various approaches taken in the prior art to provide test structure. The present invention is based on the recognition that the primary need for such test structure is in conjunction with a prospective purchaser wishing to either see the operation of a proposed purchased device and/or to be sure that the device does, in fact, operate. As such, once the item or device is purchased there is no longer such a need for the test structure. Bearing this recognition in mind, the present invention provides a test button which is separate and distinct from the device itself. As a result, it is not necessary to have the device itself incorporate its own test switch as is done in one of the prior art approaches and it is not necessary to have the on switch capable of two different types of actuating movements such as a pressing inward or a sliding as is done in other prior art approaches. Instead, the test button of the present invention could be utilized with devices such as powered toothbrushes particularly of the rocker switch type devices without requiring any modification of the device itself. Instead, the modification is made in the packaging of the device wherein the separate test button is located in a package compartment that would place the test button juxtaposed both the on switch and the off switch so that by pressing against the compartment the test button would be pressed against the on and off switch providing for only momentary actuation of the device while the test button remains pressed and assuring that the device is inactivated upon release of the pressure. Accordingly, the prospective purchaser would use the same pressing motion for test purposes as would be used for both turning the device on and turning the device off. Once the device has been purchased and removed from the package the test button could be discarded since it would have achieved its intended purpose.

What is claimed is:

1. A powered operating device disposed within a package, comprising:
   a movable section,
   a power source,
   a power transmitting structure for transmitting power from the source to the movable section to cause the movable section to move,
   a switch structure having an on position for activating the power transmitting structure, the switch structure further having an off position for inactivating the power transmitting structure, wherein the switch structure remains in a continuous operation condition until inactivated by the actuation at said off position,
   a test feature that is implemented through said package and disposed for simultaneously contacting both said on position and said off position upon a user applying pressure to said test feature,
   said test feature being normally located in a position that does not apply pressure to said on position, and the application of pressure against said test feature causing activation of said switch structure to cause said movable section to move to verify the operability of said powered operating device and the release of pressure against said test feature causing said switch structure to be immediately in its off condition and cease operation of said movable section after the operability has been confirmed.

2. The device of claim 1 wherein said switch structure includes a rocker spring which is selectively movable to an on condition and onto an off condition in accordance with pressure being applied against different portions of said spring, and said test feature being separate and distinct from said switch structure.

3. The device of claim 2 wherein said switch structure includes an on button and an off button selectively movable into contact with said spring, and said test feature being juxtaposed both said on button and said off button.

4. The device of claim 3 wherein said power transmitting structure includes an electrical contact pin disposed in the path of movement of said on position portion of said spring.

5. The device of claim 4 wherein said test feature is in the form of a block disposed between said package and said powered operating device and having outwardly extending posts located for respectively contacting said on activating button and said off activating button.

6. The device of claim 5 wherein said spring includes a pair of slits forming an intermediate central portion and a pair of outwardly extending portions, said central portion and said outwardly extending portions being bendable independently of each other, said spring having a movable outer end which is its on position, and a portion of said intermediate portion being the off position of said spring.

7. The device of claim 6 wherein said spring is disposed in a flat condition when pressure is applied to said test feature to apply pressure simultaneously at said on position and said off position.

8. The device of claim 7 wherein said powered operating device is a powered toothbrush.

9. The device of claim, said package having an outer wall which includes a flexible portion, and said block being mounted in said flexible portion.

10. The device of claim 9 wherein said toothbrush includes a cleaning head, said movable section being at least part of said cleaning head, said toothbrush also including a handle connected to said cleaning head, said handle being hollow, said power source being a battery in said hollow handle, and said switch structure being mounted at said hollow handle.

11. The device of claim 1 wherein said powered operating device is a powered toothbrush.

12. The device of claim 11, said package having an outer transparent wall which includes a flexible portion, and said test feature includes a block that is mounted in said flexible portion.

13. The device of claim 12 wherein said toothbrush includes a cleaning head, said movable section being at least part of said cleaning head, said toothbrush also including a handle connected to said cleaning head, said handle being hollow, said power source being a battery in said hollow handle, and said switch structure being mounted at said hollow handle.

14. A powered toothbrush device disposed within a package, comprsing:
   a movable section,
   a power source,
   a power transmitting structure for transmitting power from the power source to the movable section to cause the movable section to move,
   a switch having an on position for activating the power transmitting structure and an off position for inactivating the power transmitting structure, and
   a test feature implemented through said package that simultaneously contacts both said on position and said off position upon a user applying pressure to said test feature for momentary operation of said powered operating device, the removal of said user-applied pressure causing said switch to assume the off postion.

15. The device of claim 14 wherein said switch includes a rocker spring which is selectively movable between said on and said off conditions in accordance with pressure being applied against different portions of said spring, said test feature being separate and distinct from said switch.

16. The device of claim 15 wherein said switch includes an on button and an off button selectively movable into contact with said spring, said test feature juxtaposing both said on button and said off button.

17. The device of claim 16 wherein said test feature is in the form of a block disposed between said package and said powered operating device and having outwardly extending posts located for respectively contacting said on activating button and said off activating button.

18. The device of claim 17 said package having an outer wall which includes a flexible portion, and said block being mounted in said flexible portion.

19. The device of claim 14 further comprising a cleaning head, said movable section being at least part of said cleaning head, a hollow handle connected to said cleaning head, said power source being a battery in said hollow handle, and said switch structure being mounted at said hollow handle.

20. The device of claim 19 said package having an outer transparent wall which includes a flexible portion, and said test feature includes a block that is mounted in said flexible portion.

* * * * *